United States Patent

Coates et al.

[11] Patent Number: 5,389,294
[45] Date of Patent: Feb. 14, 1995

[54] CHLOROBENZENE DERIVATIVES

[75] Inventors: David Coates, Merley Wimborne; Simon Greenfield, Creekmoor, both of Great Britain

[73] Assignee: Merck Patent Gesellschaft mit beschrankter Haftung, Darmstadt, Germany

[21] Appl. No.: 477,525

[22] PCT Filed: May 4, 1990

[86] PCT No.: PCT/EP90/00718
§ 371 Date: Jun. 22, 1990
§ 102(e) Date: Jun. 22, 1990

[87] PCT Pub. No.: WO90/14405
PCT Pub. Date: Nov. 29, 1990

[30] Foreign Application Priority Data

May 15, 1989 [GB] United Kingdom ............ 8911104

[51] Int. Cl.$^6$ .................. C09K 19/30; C07C 26/06; G02F 1/13
[52] U.S. Cl. .................. 252/299.63; 252/299.01; 359/103; 570/182
[58] Field of Search ........... 72/299.01, 299.61, 299.62, 72/299.63, 299.65, 299.66, 299.67; 359/103; 570/182

[56] References Cited

U.S. PATENT DOCUMENTS

| | | | |
|---|---|---|---|
| 4,455,443 | 6/1984 | Takatsu et al. | 570/129 |
| 4,659,502 | 4/1987 | Fearon et al. | 252/299.61 |
| 4,871,470 | 10/1989 | Wächtler et al. | 252/299.63 |

FOREIGN PATENT DOCUMENTS 61-43694 3/1986 Japan.
62-275187 11/1987 Japan.

Primary Examiner—Shean Wu
Attorney, Agent, or Firm—Millen, White, Zelano & Branigan

[57] ABSTRACT

The invention relates to chlorobenzene derivatives of formula I

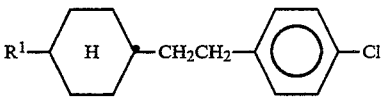

wherein
R$^1$ denotes an alkyl residue with up to 12 carbon atoms wherein one or two non-adjacent CH$_2$- groups may also be replaced by —O—, —O—CO—, —CO—O— and/or —CH=CH—.

12 Claims, No Drawings

CHLOROBENZENE DERIVATIVES

SUMMARY OF THE INVENTION

The invention relates to chlorobenzene derivatives of formula I

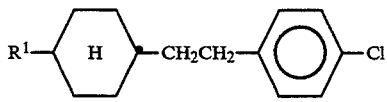

wherein $R^1$ denotes an alkyl residue with up to 12 carbon atoms wherein one or two non-adjacent $CH_2$-groups may also be replaced by —O—, —O—CO—, —CO—O— and/or —CH=CH—, and also to liquid crystalline media being a mixture of at least 2 compounds, characterized in that at least one compound is a chlorobenzene derivative according to formula I.

The invention was based on the object of discovering new stable liquid crystal or mesogenic compounds which are suitable as components of liquid crystalline media and, in particular, have advantageous values for optical and dielectric anisotropy combined with low viscosity and high nematogenity.

Trans,trans-4-(2-p-chlorophenylethyl)-4'-alkyl-bicyclohexyls and 4-(trans-4-alkylcyclohexyl)-chlorobenzenes are described as liquid crystals in European patents 0 125 563 and 0 074 608, respectively.

It has now been found that chlorobenzene derivatives of formula I are highly suitable as components of liquid crystalline media. In particular, they have especially advantageous values of elastic properties, optical and dielectric anisotropy. It is also possible to obtain stable liquid crystal phases (temperature and UV) with a broad nematic mesophase range including a good deep temperature behavior and a comparatively low viscosity with the aid of these compounds.

The compounds of the formula I can be used as the base materials from which liquid crystal media are predominantly composed; however, it is also possible for compounds of the formula I to be added to liquid crystal base materials of other classes of compounds, for example in order to influence the elastic properties and/or the dielectric and/or optical anisotropy and/or the viscosity and/or the nematic mesophase range of such a dielectric.

The compounds of the formula I are colorless in the pure state and are liquid crystalline in a temperature range which is favorably placed for electrooptical use. They are very stable towards chemicals, heat and light.

The invention thus relates to the chlorobenzene derivatives of the formula I, to liquid crystalline media with at least two liquid crystalline components, wherein at least one component is a compound of the formula I and to liquid crystal display devices containing such media.

Above and below, $R^1$ has the meaning given unless expressly indicated otherwise.

$R^1$ is preferably alkyl, alkoxy, oxaalkyl, alkanoyloxy or alkenyl and can exhibit a straight-chain or branched structure.

Alkyl or alkoxy preferably are straight-chain and have 2, 3, 4, 5, 6 or 7 C atoms. Accordingly they are preferably ethyl, propyl, butyl, pentyl, hexyl, heptyl, ethoxy, propoxy, butoxy, pentoxy, hexoxy or heptoxy, also methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxybutyl (=2-methoxyethyl), 2-, 3- or 4-oxapentyl, 2-, 3-, 4- or 5-oxahexyl, 2-, 3-, 4- 5- or 6-oxaheptyl, 2-, 3-, 4-, 5-, 6- or 7-oxaoctyl, 2-, 3-, 4-, 5-, 6-, 7-or 8-oxanonyl or 2-, 3-, 4-, 5-, 6-, 7-, 8-, or 9-oxadecyl.

Alkenyl is preferably straight-chain and has 2 or 10 C atoms. It is accordingly, in particular, vinyl, prop-1- or prop-2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5- -6- or -7-enyl, non-1-, -2-, -3-, -4-, -5-, -6-, -7- or -8-enyl or dec-1-, -2-, -3-, -4-, -5-, -6-, -7-, -8- or -9-enyl.

Compounds of the formula I containing a branched terminal group can occasionally be of importance because of an improved solubility in the customary liquid crystal base materials, but in particular as chiral doping substances if they are optically active.

Branched groups of this type as a rule contain not more than one chain branching. Preferred branched radicals are isopropyl, 2-butyl (=1-methylpropyl), isobutyl (=2-methylpropyl, 2-methylbutyl, isopentyl, (=3-methylbutyl), 2-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 2-methylhexoxy, 1-methylhexoxy, 1-methylheptoxy (=2-octyloxy), 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 4-methylheptyloxycarbonyl, 2-methylbutyryloxy, 3-methylvaleryloxy, 4-methylhexanoyloxy, 2-methyl-3-oxapentyl and 2-methyl-3-oxahexyl.

In the case of compounds with a branched terminal group $R^1$, formula I includes both the optical antipodes and racemates as well as mixtures thereof.

Of the compounds of the formula I and subformulae thereof, those in which at least one of the radicals contained therein has one of the preferred meanings given are preferred.

The compounds of the formula I are prepared by methods which are known per se, such as are described in the literature (for example in the standard works, such as Houben-Weyl, Methoden der Organischen Chemie [Methods of Organic Chemistry], Georg Thieme Verlag, Stuttgart), and in particular under reaction conditions which are known and suitable for the reactions mentioned. Variants which are known per se and are not mentioned in more detail here can also be used in this connection.

If desired, the starting materials can also be formed in situ, such that they are not isolated from the reaction mixture but are immediately reacted further to give the compounds of the formula I.

A preferred route for preparation of the compounds with m=1 is shown in the following scheme 1:

Scheme 1

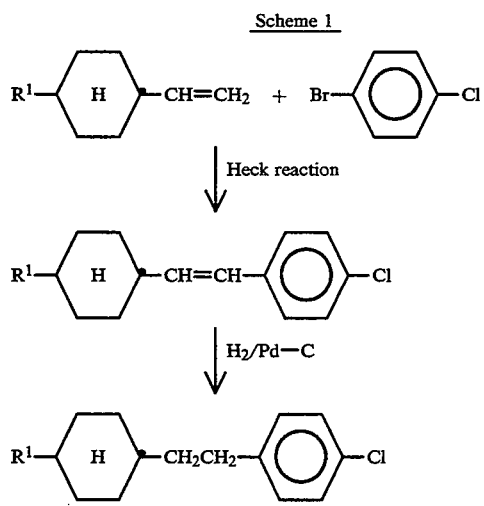

An alternative route is shown in scheme 2:

Scheme 2

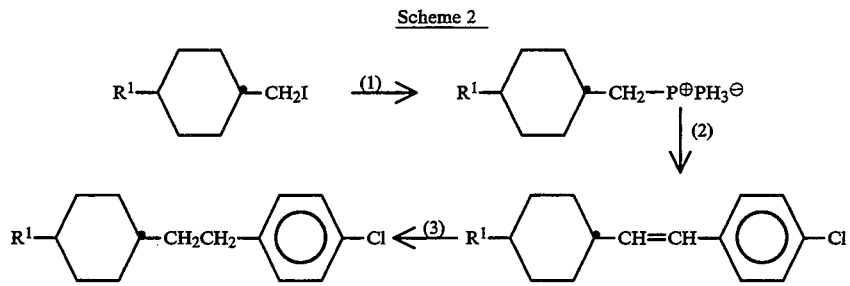

Other routes are apparent to the skilled worker. In addition it is possible to follow the above shown routes with a group being different from chloro and to introduce the desired group Cl in the final step, e.g., conversion of —NH$_2$ to Cl. All these steps and the corresponding reaction conditions are known to the skilled worker.

In addition to one or more compounds for formula I the liquid crystal media according to the invention preferably contain 2–40 components and in particular 4–30 components. Liquid crystal media being composed of one or more compounds of formula I and 7–25 other components are especially preferred.

These additional components are preferably chosen from the nematic or nematogenic (monotropic or isotropic) substances; in particular from the classes of azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenyl-benzoates, cyclohexylphenyl cyclohexanecarboxylates, cyclohexylphenyl cyclohexylcyclohexanecarboxylates, phenylcyclohexanes, cyclohexylbiphenyls, phenylcyclohexylcyclohexanes, cyclohexylcyclohexanes, cyclohexylcyclohexenes, cyclohexylcyclohexylcyclohexene, 1,4-bis-cyclohexylbenzenes, 4,4'-bis-cyclohexyl-biphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenyl-cyclohexyl)ethanes, 1-cyclohexyl-2-biphenylethanes, 1-phenyl-2-cyclohexyl-phenylethanes, optionally halogenated stilbenes, benzyl phenyl ethers, tolanes and substituted cinnamic acids.

The 1,4-phenylene groups of these compounds may be fluorinated.

The most important compounds which are possible constituents of liquid crystal media according to the invention can be characterized by the formalae 1, 2, 3, 4 and 5:

$$R'—L—U—R'' \quad \quad 1$$

$$R'—L—COO—U—R'' \quad \quad 2$$

$$R'—L—OOC—U—R'' \quad \quad 3$$

$$R'—L—CH_2CH_2—U—R'' \quad \quad 4$$

$$R'—L—C\equiv C—U—R'' \quad \quad 5$$

In the formulae 1, 2, 3, 4 and 5 L and U may be equal or different from each other. L and U independently from each other denote a bivalent residue selected from the group consisting of —Phe—, —Cyc—, —Phe—Phe—, —Phe—Cyc—, —Cyc—Cyc—, —Pyr—, —Dio—, —G—Phe—, —G—Cyc— and their mirror images; in this compilation of residues Phe denotes unsubstituted or fluorinated 1,4-phenylene, Cyc denotes trans- 1,4-cyclohexenylene or 1,4-cyclohexenylen, Pyr denotes pyrimidine-2,5-diyl or pyridine-2,5-diyl, Dio denotes 1,3-dioxane-2,5-diyl and G denotes 2-(trans-1,4-cyclohexyl)-ethyl, pyrimidine-2,5-diyl, pyridine-2,5-diyl or 1,3-dioxane-2,5-diyl.

One of the residues L and U is preferably Cyc, Phe or Pyr. U preferably denotes Cyc, Phe or Phe-Cyc. The liquid crystal media according to the invention preferably contain one or more components selected from the compounds of formulae 1, 2, 3, 4 and 5 with L and U meaning Cyc, Phe and Pyr, said liquid crystal media further containing at the same time one ore more components selected from the compounds of formulae 1, 2, 3, 4 and 5 with one of the residues L and U denoting Cyc, Phe and Pyr and the other residue being selected from the group consisting of —Phe—Phe—, —Phe—Cyc—, —Cyc—Cyc—, —G—Cyc—, said liquid crystal media containing in addition to this optionally one or more components selected from the compounds of formulae 1, 2, 3, 4 and 5 with L and U being selected from the group consisting of —Phe—Cyc—, —Cyc—Cyc—, —G—Phe— and—G—Cyc.

In a preferred subgroup of the compounds of formulae 1, 2, 3, 4 and 5 (subgroup 1) R' and R'' are independently from each other alkyl, alkenyl, alkoxy, alkenoxy with up to 8 carbon atoms. R' and R'' differ from one another in most of these compounds, one of the residues usually being alkyl or alkenyl. In another preferred subgroup of the compounds of formulae 1, 2, 3, 4 and 5

(subgroup 2) R" denotes —CN, —CF$_3$, —F, —Cl or —NCS while R' has the meaning indicated in subgroup 1 and is preferably alkyl or alkenyl. Other variants of the envisaged substituents in the compounds of formulae 1, 2, 3, 4 and 5 are also customary. Many such substances are commercially available. All these substances are obtainable by methods which are known from the literature or by analogous methods.

The liquid crystal media according to the invention preferably contain in addition to components selected from subgroup 1 also components of subgroup 2, the percentage of these components being as follows:

subgroup 1: 20 to 90% in particular 30 to 90%
subgroup 2: 10 to 50% in particular 10 to 50%

In these liquid crystal media the percentages of the compounds according to the invention and the compounds of subgroup 1 and 2 may add up to give 100%

The media according to the invention preferably contain 1 to 40%, in particular 5 to 30% of the compounds according to the invention. Media containing more than 40%, in particular 45 to 90% of the compounds according to the invention are further preferred. The media contain preferably 3, 4 or 5 compounds according to the invention.

The media according to the invention are prepared in a manner which is customary per se. As a rule, the components are dissolved in one another, advantageously at elevated temperature. The liquid crystal media according to the invention can be modified by suitable additives so that they can be used in all the types of liquid crystal display devices. Such additives are known to the expert and are described in detail in the literature (H. Kelker/R. Hatz, Handbook of Liquid Crystals, Verlag Chemie, Weinheim, 1980). For example, it is possible to add pleochroic dyestuffs to prepare colored guest-host systems or substances for modifying the dielectric anisotropy, the viscosity and/or the orientation of the nematic phases.

EXAMPLES

The following examples are to be construed as merely illustrative and not limitative. m.p.=melting point, c.p.=clearing point. In the foregoing and in the following all parts and percentages are by weight and the temperatures are set forth in degrees Celsius. "Customary work-up" means that water is added, the mixture is extracted with methylene chloride, the organic phase is seperated off, dried and evaporated, and the product is purified by crystallization and/or chromatography.

Further are:
C: crystalline-solid state, S: smectic phase (the index denoting the typ of smectic phase), N: nematic phase, Ch: cholesteric phase, I: isotropic phase. The number being embraced by 2 of these symbols denotes the temperature of phase change.

EXAMPLES FOR PRODUCTION

EXAMPLE 1

Step 1 trans-4-Pentylcyclohexyl methyl iodide (10 g), triphenylphosphine (9.8 g) and toluene (30 ml) were heated at 100° C. for 3 days. After evaporation of the solvent the oil was dissolved in dichloromethane and a white solid precipitated using diethyl ether.

Step 2

The phosphonium salt from step 1 (12.3 g) was stirred with THF (35 ml) under a nitrogen atmosphere. Butyl lithium (1.6 m, 18 ml) was added dropwise and the mixture stirred for 1 hour. 4-Chlorobenzaldehyde (4.0 g) in THF (10 ml) was added and the mixture stirred overnight, it was than poured into water, extracted with dichloromethane and the dichloromethane then evaporated off. The resulting solid was extracted with petroleum spirit and then columned.

Step 3

The alkene from step 2 was hydrogenated in ethyl acetate over Pd/C until no more H$_2$ was taken up. After customary work-up trans-4-(2-p-chlorophenyl-ethyl)-pentylcyclohexane is obtained, m.p. 20°, c.p. 16,4°.

EXAMPLES 2 TO 6

The following compounds are prepared analogously:

(2) trans-4-(2-P-chlorophenyl-ethyl)-ethylcyclohexane (3) trans-4-(2-P-chlorophenyl-ethyl)-butylcyclohexane (4) trans-4-(2-P-chlorophenyl-ethyl)-propylcyclohexane, m.p. 26°, c.p. 10°

(5) trans-4-(2-p-chlorophenyl-ethyl)-hexylcyclohexane (6) trans-4-(2-p-chlorophenyl-ethyl)-heptylcyclohexane

EXAMPLES OF COMPOSITIONS

EXAMPLE 1

A composition is prepared consisting of 85% of a mixture A and 15% of trans-4-(2-p-chlorophenyl-ethyl)-n-pentylcyclohexane. This composition shows a c.p. of 60.5°, an optical anisotropy of 0.1065 and a viscosity at 20° of 12.55 cSt. Mixture A contains 22% of trans-1-p-ethylphenyl-4-propylcyclohexane, 20% of trans-1-p-methoxyphenyl-4-propylcyclohexane, 15% of trans-1-p-ethoxyphenyl-4-propylcyclohexane, 19% of 4-ethyl-4'-(trans-4-propylcyclohexyl)-biphenyl, 14% of 4-ethyl-4'-(trans-4-pentylcyclohexyl)-biphenyl, 5% of 4,4'-bis-(trans-4-propylcyclohexyl)-biphenyl and 5% of 4-(trans-4-pentylcyclohexyl)-4'-(trans-4-propylcyclohexyl)biphenyl.

EXAMPLE 2

A composition of 70% of mixtures A and 30% of trans-4-(2-p-chlorophenyl-ethyl)-n-pentylcyclohexane shows a c.p. of 50.8°.

We claim:
1. A chlorobenzene compound of formula I

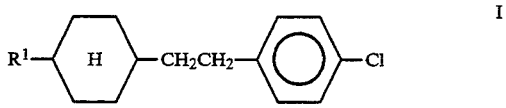

wherein
R$^1$ is an alkyl residue with up to 12 carbon atoms or an alkyl residue with of up to 12 carbon atoms wherein one or two non-adjacent CH$_2$- groups is replaced by —O—, —O—CO—, —CO—O— and-/or —CH=CH—.

2. In a liquid crystalline medium comprising a mixture of at least two compounds, the improvement wherein at least one compound is a chlorobenzene compound according to formula I

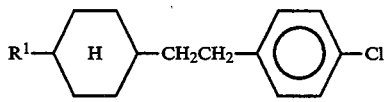

$R^1$ is an alkyl residue with up to 12 carbon atoms or an alkyl residue with up to 12 carbon atoms wherein one or two non-adjacent $CH_2$- groups is replaced by —O—, —O—CO—, —CO—O— and/or —CH=CH—.

3. In a liquid crystal display device containing a liquid crystal medium, the improvement wherein said liquid crystalline medium is a medium according to claim 2.

4. In an electrooptical display device containing a liquid crystal medium, the improvement wherein said liquid crystalline medium is a medium according to claim 2.

5. A compound according to claim 1, wherein $R^1$ is a straight chain alkyl having 2–7 C atoms.

6. A compound according to claim 1, wherein $R^1$ is a straight chain alkoxy having 2–7 C atoms.

7. A compound according to claim 1, wherein $R^1$ is oxalkyl.

8. A compound according to claim 1, wherein $R^1$ is straight chain alkenyl having 2–10 C atoms.

9. A compound according to claim 1, wherein $R^1$ is a branched group.

10. A liquid crystalline medium according to claim 2, wherein said medium contains 1–40% of one or more compounds according to formula I.

11. A liquid crystalline medium according to claim 2, wherein said medium contains 45–90% of one or more compounds according to formula I.

12. A liquid crystalline medium according to claim 2, wherein said medium contains 3–5 compounds according to formula I.

* * * * *

UNITED STATES PATENT AND TRADEMARK OFFICE
CERTIFICATE OF CORRECTION

PATENT NO. : 5,389,294
DATED : Feb 14, 1995
INVENTOR(S) : David COATES et al.

It is certified that error appears in the above-indentified patent and that said Letters Patent is hereby corrected as shown below:

Title page; Item [21], Application Number: Change "477,525" to - - 499,525 - -.

Signed and Sealed this

Thirteenth Day of June, 1995

Attest:

BRUCE LEHMAN

Attesting Officer          Commissioner of Patents and Trademarks